US010660561B2

(12) United States Patent
Bao et al.

(10) Patent No.: US 10,660,561 B2
(45) Date of Patent: May 26, 2020

(54) PERSONAL SKIN SCANNER SYSTEM

(71) Applicant: Massachusetts Institute of Technology, Cambridge, MA (US)

(72) Inventors: Jie Bao, Cambridge, MA (US); Moungi G. Bawendi, Cambridge, MA (US)

(73) Assignee: MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 49 days.

(21) Appl. No.: 13/775,780

(22) Filed: Feb. 25, 2013

(65) Prior Publication Data
US 2013/0225969 A1    Aug. 29, 2013

Related U.S. Application Data

(60) Provisional application No. 61/603,272, filed on Feb. 25, 2012.

(51) Int. Cl.
*A61B 5/05*    (2006.01)
*A61B 5/00*    (2006.01)

(52) U.S. Cl.
CPC ............ *A61B 5/444* (2013.01); *A61B 5/0062* (2013.01); *A61B 5/0077* (2013.01)

(58) Field of Classification Search
None
See application file for complete search history.

(56) References Cited

U.S. PATENT DOCUMENTS

| | | | |
|---|---|---|---|
| 6,215,893 B1 | 4/2001 | Leshem | |
| 6,238,345 B1 * | 5/2001 | Wissler et al. | 600/443 |
| 6,427,022 B1 | 7/2002 | Craine | |
| 6,567,682 B1 * | 5/2003 | Osterweil | A61B 5/0059 348/77 |
| 7,657,101 B2 | 2/2010 | Christiansen | |
| 2002/0026391 A1 * | 2/2002 | Laster et al. | 705/28 |
| 2005/0154382 A1 * | 7/2005 | Altshuler et al. | 606/9 |
| 2005/0238200 A1 * | 10/2005 | Gupta et al. | 382/103 |
| 2006/0075422 A1 * | 4/2006 | Choi | G01S 3/7864 725/18 |
| 2006/0210132 A1 * | 9/2006 | Christiansen et al. | 382/128 |
| 2007/0035815 A1 * | 2/2007 | Edgar et al. | 359/359 |
| 2007/0165141 A1 * | 7/2007 | Srinivas et al. | 348/571 |
| 2008/0319322 A1 * | 12/2008 | Herrmann et al. | 600/476 |
| 2010/0040279 A1 * | 2/2010 | Yoon et al. | 382/153 |
| 2011/0298909 A1 * | 12/2011 | Ando | H04N 5/2256 348/77 |
| 2012/0149049 A1 * | 6/2012 | Torres et al. | 435/29 |
| 2012/0163656 A1 * | 6/2012 | Wang et al. | 382/103 |
| 2012/0226268 A1 * | 9/2012 | Liu et al. | 606/9 |
| 2013/0131985 A1 * | 5/2013 | Weiland et al. | 701/516 |

OTHER PUBLICATIONS

International Search Report and Written Opinion from PCT/US2013/27617 dated May 6, 2013.

* cited by examiner

*Primary Examiner* — Joel F Brutus

(74) *Attorney, Agent, or Firm* — Steptoe & Johnson LLP

(57) ABSTRACT

A personal skin lesion scanner system that can facilitate early detection of changes in the appearance of a user's skin is described. The system includes a handheld device for home use, to record images of a user's skin, and software for analyzing the images. The system can automatically detect changes in the user's skin, such as changes in the size, shape, or color of a skin lesion, and alert the user if any changes are detected.

19 Claims, 2 Drawing Sheets

PERSONAL SKIN SCANNER SYSTEM

CLAIM OF PRIORITY

This application claims priority to provisional U.S. Patent Application No. 61/603,272, filed Feb. 25, 2012, which is incorporated by reference in its entirety.

FEDERALLY SPONSORED RESEARCH OR DEVELOPMENT

This invention was made with government support under Grant No. W911NF-07-D-0004 awarded by the Army Research Office. The government has certain rights in the invention.

TECHNICAL FIELD

This invention relates to a personal skin scanner system configured to identify lesions.

BACKGROUND

Each year, 3.5 million Americans are diagnosed with skin cancers, and 20% of the entire nation's population will get skin cancer in the course of a lifetime. There are more new cases of skin cancer annually than the combined incidence of cancers of the breast, prostate, lung and colon. Over the past 31 years, more people have had skin cancer than all other cancers combined.

Many skin cancers can be detected by monitoring changes in skin lesions. If detected early, the 5-year survival rate of melanoma is 98%; however, that rate drops to 62% and 16% for later stages when diseases are spread regionally and distantly, respectively. About 90 percent of nonmelanoma skin cancers are associated with exposure to ultraviolet (UV) radiation from the sun. Thus there is a need to facilitate monitoring skin lesions, particularly early detection of formation of skin lesions or changes in skin lesions.

SUMMARY

In one aspect, a personal skin scanner system includes a handheld scanner device including: a skin contact surface; a primary camera spaced a distance apart from the skin contact surface, such that when the skin contact surface is contacted to a user's skin, the primary camera can record a close up image of a desired area of the user's skin; and an illumination source spaced a distance apart from the skin contact surface, such that when the skin contact surface is contacted to a user's skin the illumination source can illuminate the desired area of the user's skin.

The system can further include a computer system operably connected to the scanner device via a data connection, and provided with computer-readable instructions configured to cause the system to record and store an image of one or more desired areas of the user's skin.

The computer-readable instructions can be further configured to cause the system to record and store a first plurality of images of one or more desired areas of the user's skin at an earlier time; and to cause the system to record and store a second plurality of images of the one or more desired areas of the user's skin at a later time. The computer-readable instructions can be further configured to cause the system to compare earlier and later images of the one or more desired areas of the user's skin. The computer-readable instructions can be further configured to cause the system to detect changes each of the one or more desired areas of the user's skin based on the comparison.

The computer-readable instructions can be further configured to cause the system to locate a mark or lesion on the user's skin. The computer-readable instructions can be further configured to cause the system to record and store images of overlapping areas of the user's skin. The computer-readable instructions can be further configured to cause the system to create a mosaic image of the user's skin from the images of overlapping areas of the user's skin. The system can further include a secondary camera configured to record an image of a part of the user's body, and the computer-readable instructions can be further configured to cause the system to use the secondary camera and a SLAM algorithm to locate a mark or lesion on the user's skin.

The system can further include a second primary camera spaced a distance apart from the skin contact surface, such that when the skin contact surface is contacted to a user's skin, the second primary camera can record a second close up image of the desired area of the user's skin from a different perspective. The computer-readable instructions can be further configured to cause the system to construct a 3D image based on the first and second images of the desired area of the user's skin.

The data connection can be a wireless data connection. The skin contact surface can include one or more rollers configured to measure a direction and a distance traveled over a user's skin. The illumination source can include one or more LEDs.

In another aspect, a method of detecting changes in a person's skin includes contacting a skin contact surface of a handheld scanner device to a user's skin; recording and storing a first plurality of images of one or more desired areas of the user's skin at an earlier time from the handheld scanner device in a personal skin scanner system; recording and storing a second plurality of images of the one or more desired areas of the user's skin at a later time from the handheld scanner device in the personal skin scanner system; comparing earlier and later images of the one or more desired areas of the user's skin in the personal skin scanner system; detecting changes each of the one or more desired areas of the user's skin based on the comparison; and alerting the user if any changes are detected.

The method can further include providing a handheld scanner device including: a skin contact surface; a primary camera spaced a distance apart from the skin contact surface, such that when the skin contact surface is contacted to a user's skin, the primary camera can record a close up image of a desired area of the user's skin; an illumination source spaced a distance apart from the skin contact surface, such that when the skin contact surface is contacted to a user's skin the illumination source can illuminate the desired area of the user's skin; and a computer system operably connected to the scanner device via a data connection, and provided with computer-readable instructions configured to cause the system to record and store a plurality of images of one or more desired areas of the user's skin.

Recording and storing a plurality of images can include moving the scanner device over the user's skin while the skin contact surface remains in contact with the user's skin. The method can further include locating a mark or lesion on the user's skin based on the first or second plurality of images. The method can further include recording and storing a first plurality of images of one or more desired areas of the user's skin includes recording and storing images of overlapping areas of the user's skin. The method can further include creating a mosaic image of the user's skin from the images of overlapping areas of the user's skin. The scanner device can further include a secondary camera configured to record an image of a part of the user's body, and the method can further include using the secondary camera and a SLAM algorithm to locate a mark or lesion on the user's skin.

The skin contact surface can include one or more rollers configured to measure a direction and a distance traveled over a user's skin and the method can further include measuring a direction and a distance traveled by the scanner device over the user's skin.

The scanner device can include a second primary camera spaced a distance apart from the skin contact surface, such that when the skin contact surface is contacted to a user's skin, the second primary camera can record a second close up image of the desired area of the user's skin from a different perspective, and the method can further include constructing a 3D image based on the first and second images of the desired area of the user's skin.

Other aspects, embodiments, and features will be apparent from the following description, the drawings, and the claims.

DETAILED DESCRIPTION

Currently, skin cancer screening for most individuals is done at a doctor's office or dermatology clinic once a year or less frequently. Patients are visually inspected (typically under the help of an optical microscope, essentially an illuminated magnifying glass in most cases) for atypical lesions. This method may not be very effective for identifying newly developed lesions while they are small or difficult to discern. It may also not be very effective for identifying rapidly changing lesions while they are small or difficult to discern. These changes—appearance of new lesions, and/or rapid changes in lesions—can have high diagnostic value for detecting malignancies.

A personal skin lesion scanner system can allow a user to take frequent, high quality scans of his or her skin, record the characteristics of any lesions, and monitor him- or herself for the appearance of new lesions and/or changes in existing lesions, thus facilitating early detection of potential malignancies. The system includes a scanner device and associated software. The device can be handheld, easy to use in the home, without the need for extensive training. Being suitable for home use, the user can scan his or her skin in privacy, at any time, as often as desired, without the need for making appointments, and at no additional cost. It can provide 2D and/or 3D views of skin lesions suitable for record keeping and if desired, for inspection by health care professionals, e.g., for diagnostic purposes. The software can record and store images of the user's skin, and by automated image analysis, detect changes in the condition of the user's skin. Automated image analysis of high resolution images, recorded frequently, can provided sensitive and early detection of changes in a user's skin, allowing early detection of potentially dangerous lesions. Early detection can lead to better medical outcomes at lower cost than if the same lesion were detected at a later stage.

Figure 1:
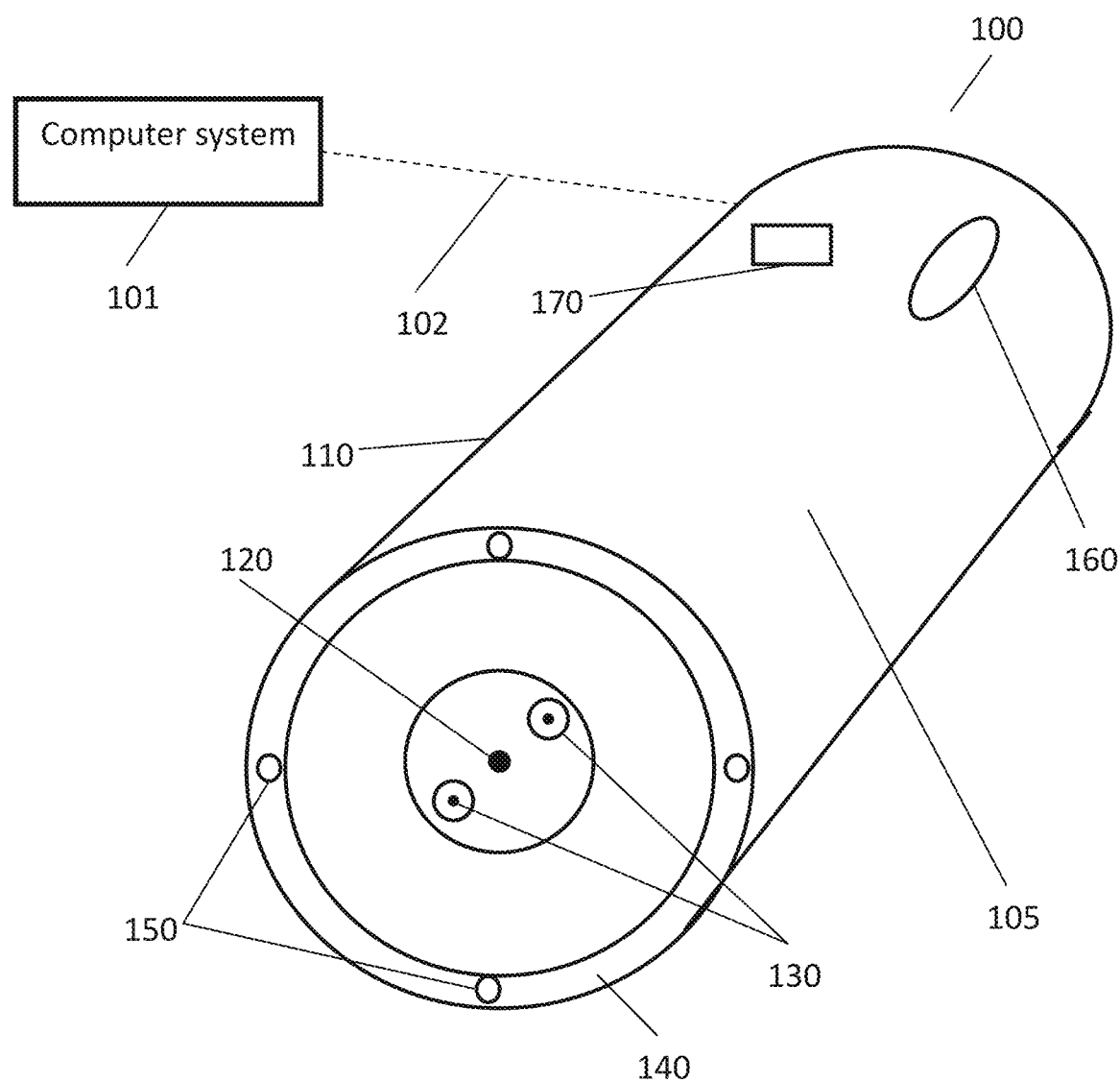
FIG. 1 is a schematic representation of a personal lesion scanner system.

Referring to FIG. 1, a personal skin lesion scanning system 100 includes a computer system 101 with a data connection 102 to personal skin lesion scanner 105. Computer 101 can take any suitable form, e.g., desktop computer, laptop or tablet computer, smartphone, or a dedicated console. Computer 101 is preferably internet-connected to allow various operations, such as data communication, remote data storage, and interaction with remote computers (e.g., cloud computing). Computer 101 is provided with software (computer-readable instructions) for operating the system, e.g., controlling functions of the scanner 105, storage and analysis of images recorded by the scanner, and user interaction.

Personal skin lesion scanner 105 includes housing 110, primary camera 120, illumination source 130, and skin contact surface 140 which optionally includes rollers 150, user control 160, and electronics connector 170. As described in further detail below, scanner 105 can include more than one camera, which can be used to record multiple images (still and/or video) of the same area of skin, e.g., from different angles and/or in different resolutions. In use, skin contact surface 140 is held in contact with a user's skin. Housing 110 is configured to be comfortably handheld and manipulated by the user so that the user can bring the scanner to any area of his or her body. Housing 110 is also configured such that when skin contact surface 140 is in contact with a user's skin, illumination source 130 and primary camera 120 are directed toward the user's skin, and held at a suitable distance apart from the user's skin, such that the primary camera can take high quality, in focus, and well-lit close up images of the user's skin, e.g., at high magnification. For example, the primary camera and/or illumination source can be recessed in the housing relative to the skin contact surface. The primary camera can record one or more images of the user's skin when the user control 160 is operated. The camera is preferably configured to record high resolution images of a small area (e.g., more than 10 $cm^2$, 10 $cm^2$ or less, 5 $cm^2$ or less, 1 $cm^2$ or less, 0.5 $cm^2$ or less, or 0.1 $cm^2$ or less. Optional rollers 150 can facilitate smooth travel of the scanner over the user's skin, and can track motion of the scanner over the user's skin by recording direction and distance traveled.

Scanner 105 can optionally include a second primary camera (121). The second primary camera can be configured to take high quality, in focus, and well-lit close up images of the user's skin, e.g., at high magnification. The first and second primary cameras can be configured to take images of the same area of the user's skin but from different angles. The cameras can take still and/or moving images (videos) of the user's skin. In some embodiments, an additional, secondary camera is configured to take images of the user's skin at a lower resolution than the first camera. The primary and secondary cameras can be configured to record images of the same area at different scales, e.g., the secondary camera recording an image of a relatively larger area at lower magnification and/or resolution, and the primary camera(s) recording an image of a relatively smaller area at higher magnification and/or resolution. Scanner 105 can include more than one primary camera which are configured together to record images of the same area from different perspectives, such that the images can be used to extract information about the 3D size and shape of a skin lesion.

Illumination source 130 is configured to provide good, reproducible, unidirectional or multidirectional lighting of the area to be imaged. Illumination is preferably provided by one or more LEDs such as white light LEDs, although other illumination sources can be suitable.

Scanner 105 can include an internal power source, such as a battery. Preferably the battery is a rechargeable battery such as a lithium battery, although other batteries including disposable batteries are contemplated. A rechargeable battery can be recharged by connecting scanner 105 to an external power supply via electronics connector 170, which can be, for example, a USB connector, or can include a dedicated power connection (e.g., a connection for supplying DC power to the scanner). In some embodiments, the scanner does not include an internal power source but is powered by an external power source, such as an external DC power supply.

Scanner 105 also includes a data recording and storage system to record images of the user's skin and associated information (e.g., a user identity, date, time, or any other relevant information). Any conventional data recording and storage system may be used. Flash memory can be a suitable choice. Alternatively or in conjunction with onboard device memory, data (including images of the user's skin) can be transmitted (e.g., by wireless or wired communication) to an external storage (e.g., computer, smartphone, or the like).

Scanner 105 includes a data communication connection for communicating data between scanner 105 and computer 104. Any wireless or wired data communication connection can be used, though wireless connections such as Bluetooth or WiFi can be preferred. In some cases, the data communication connection can be integrated with electronics connector 170, e.g., when electronics connector 170 is a USB port.

Internal to housing 110 are systems to control the various functions of scanner 100, including power control, camera 120, illumination source 130, user control 160, and electronics connector 170. The system can also be provided with an extension handle that attaches to scanner 105 and the user can hold and manipulate. The extension handle aids the user in scanning hard-to-reach areas of his or her skin without the need for another's assistance.

System 100 records and stores images of the user's skin, and further analyzes those images. The system makes comparisons of multiple images of the same area of the user's skin recorded at different times, so as to recognize the appearance of new skin lesions or changes in existing lesions.

System 100 includes various modules for performing and coordinating the functions of the system. The modules include hardware, software, or both, and are operably connected to permit the system to perform the desired functions. For example, an image recording module including a camera and image storing component is operably connected to a software-based image analysis module so that the image analysis module can retrieve and analyze the images recorded and stored by the image recording module. Among the various modules in the system are at least the following: an image recording module including one or more primary and/or secondary cameras and an image storing component; an image analysis module for analyzing and comparing images recorded and/or stored by the system; an image locating module for identifying the location on the user's body where an image was recorded, including an image comparison component and an optional hardware scanner locating component; a user interface module to permit the user to control the system via inputs and receive outputs from the system. The modules described here can include additional components; for example, the image recording module can include an illumination source.

Once a set of images has been recorded, the system performs automated image analysis to identify the marks or lesions on the user's skin. Various properties of the marks or lesions are then measured and recorded, including but not limited to the 2D and/or 3D size and shape (e.g., border contours), color, or other properties. The identity of a mark or lesion can be made with reference to its location on a user's skin (e.g., the location on the body, such as "upper left arm" or "right side of back below shoulder blade") and/or with reference to its location relative to other marks or lesions on the user's skin.

The properties of each mark or lesion are recorded along with the date and time when the image was recorded, and the user who is being scanned. Images (and/or properties measured from the images) recorded in each new scan are compared to images (and/or properties) of corresponding areas of skin recorded in earlier scans. In this way, any changes in properties of a particular area of skin, mark, or lesion can be readily detected.

In order that the system make accurate comparisons, it must assure that the comparisons are made between the same locations, e.g., that an earlier image of a particular lesion is compared to a later image of the same lesion. Because the system is meant for home use, it should not require the user to perform complex operations to locate the images. Locating images is also important so that the system can inform the user where on his or her body the system has detected a change on the user's skin. Thus locating an image can have two facets: identifying the absolute location on the user's skin where the image was recorded, and identifying the location and orientation of an image relative to other images the system has previously recorded.

Figure 2:
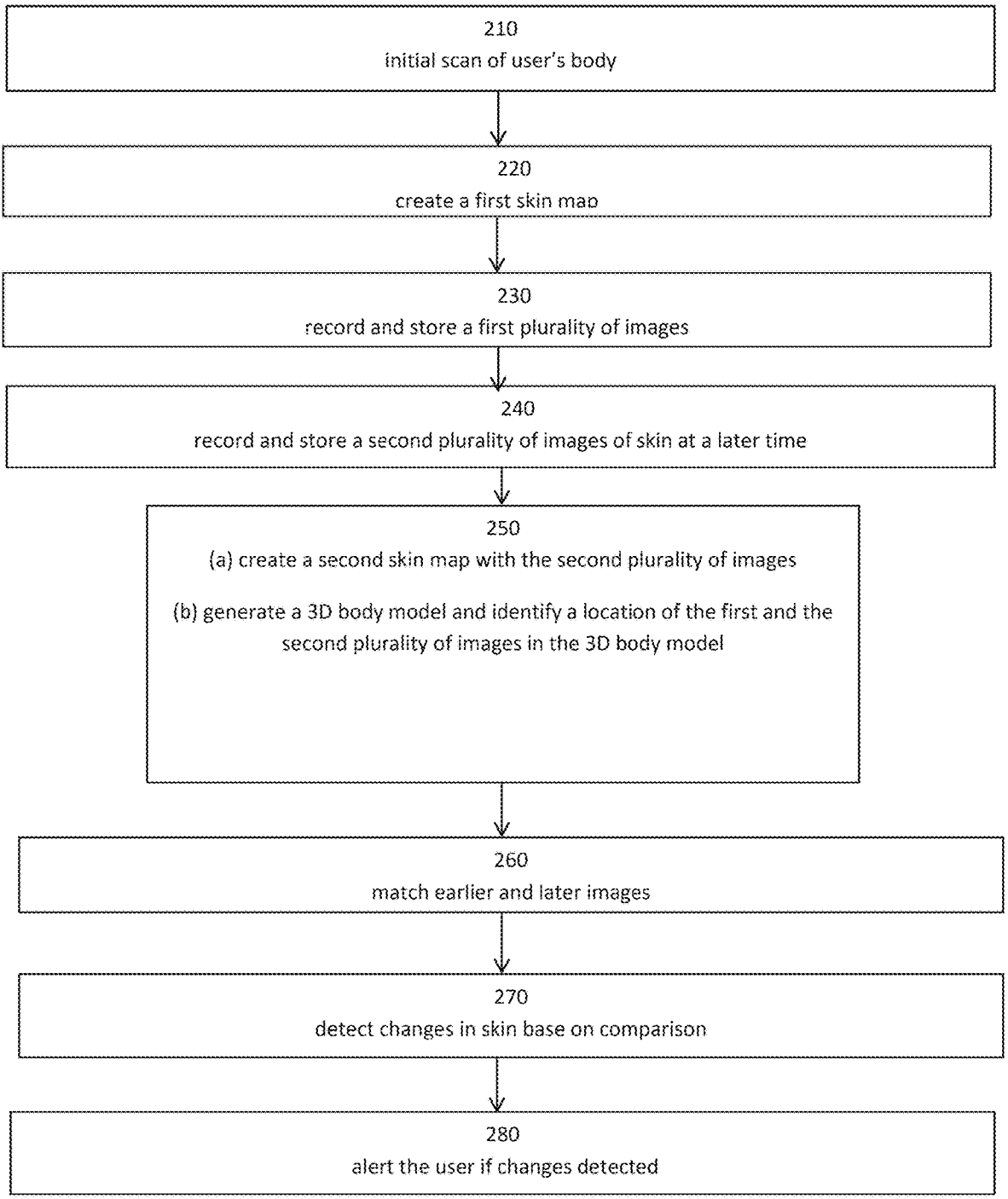
FIG. 2 is a schematic representation of the claimed methods.

The system can create a map of the user's skin, which can also be referred to as a skin map, body map, or mole map. In creating the skin map, the system can record multiple individual images of the user's skin (typically covering a large area of skin, such as one or more limbs, the torso, the full upper or lower body, or a combination of these, up to and including the entire body). Referring to FIG. 2, in a typical use, the system will create the skin map of a particular user during an initial scan 210 of the user's entire body. The skin map is made 220 by stitching together multiple images to form a mosaic image. Stitching can rely on two sources of information to interrelate the various images. First, a pattern recognition algorithm finds where two or more images overlap. For example, the system can first identify one or more recognizable skin features, such as skin lines (e.g., fingerprints) or moles (which for the most part do not change rapidly), or other fixed registration points, such as, for example, the navel or nipples. Identifying the skin features can optionally involve the aid of user input. These features or registration points allow the system to orient the recorded images 230 to a generic body shape, so that the system associates each image with its absolute location on the body (e.g., that a particular image was recorded on the anterior of the left leg above the knee, or wherever the particular image was recorded). Second, relative positional information is provided by the scanner wheels. With this information, the system can create the mosaic from fewer images having a smaller degree of overlap than would be required without such information. The user can move the scanner over his or her skin in a continuous motion, thus information provided by the wheels can tell the system that certain images are of adjacent areas, facilitating the creation of the mosaic image. The times the images were recorded is another important indicator of adjacent images.

The system can determine the location of the images on the user's skin via pattern recognition. These features or registration points allow the system to orient the recorded images to a generic body shape, so that the system associates each image with its absolute location on the body (e.g., that a particular image was recorded on the anterior of the left leg above the knee, or wherever the particular image was recorded). In subsequent scans, whether of the entire body, one or more local regions, or of one or more points, the system must determine which earlier images correspond to the same skin areas as the newly recorded images 240. In other words, the system must align the newer images with a previously created skin map (which can be a full body skin map or a partial skin map). In doing so, the system can align newly recorded images to a previously created skin map, or create a new skin map 250a from scratch and then align the new skin map to a previously created skin map. Alignment to a previously created skin map also involves pattern recognition for example, based on the same features that were used to connect individual pictures when creating the skin map. In a similar principle, the system can recognize the part of the map that the newer images belong to. Images taken of the same area of the skin recorded at different times may not completely overlap. However, since previously all the individual pictures were connected together to form a complete skin map, the system can match a new image to the appropriate corresponding portion of the earlier skin map 260. Thus the newer image may align with portions of several different earlier images that were used in making up the skin map. Alignment can also be facilitated by information provided from the wheels.

At this point, the system would have the following information: (1) at least one previous skin map (whole body or partial body) as a baseline; (2) one or more newer images of one or more areas of skin, up to the whole body; and (3) the correspondence between the older and newer images, so that the system can make comparisons of the same area of skin at different times 270. The system is now ready to perform the comparison and look for changes. (Previously, when determining the correspondence, the system sought matching images based on the unchanging features, and changes in features were ignored). Having found earlier and later images of the same area of skin, the system now compares them to find any changes. If there has been a change, for example, the appearance of a new feature (e.g., skin lesion), or a change in the size, shape, color, or other property of a feature such as a skin lesion, the change will be noticed by the system, and the user alerted 290.

Having alerted the user to a change, the system must also inform the user know where on his or her body the changed image is located. The location functions can be performed at the time an initial skin map is made, and/or during subsequent scans. The location function can be carried out by a simultaneous location and mapping (SLAM) method. The SLAM method can rely on images recorded with a secondary camera, one that recorded images at a lower resolution and/or from a position more elevated from the skin than the primary camera.

SLAM also relates the location of an image taken by the skin-facing camera to the map created by images from the second camera. Unlike the 3D body model generated from the secondary camera, the skin map generated from the skin-facing camera shows fine details of the user's skin and how those fine details are connected. Looking at a particular close-up image, e.g. of a skin lesion, the user may not be able to determine where on his or her body that lesion is located. The relationship between the 3D body model and the skin map allows the system and user to identify where on the body a particular image was recorded. Thus, the user can be presented with a close-up image of a skin lesion and a location of that image, so that he or she can readily look at his or her own skin to inspect the lesion directly.

While the primary, high resolution camera is recording images to build a skin map 250a (e.g., during an initial whole body scan), one or more secondary cameras can be recording images to create a 3D body model 250b. The system can therefore register each high resolution image recorded by the primary camera to a global location on the 3D body model. Thus, two separate are created simultaneously, linked by virtue of the time stamps on the high- and low-resolution images. The SLAM overview map can show a user the 3D body model, and at any given time, show where the camera is on the 3D body model. The high resolution skin images are located on the SLAM map by virtue of the times when the high- and low-resolution images were recorded.

Preferably, the correspondence need only be performed once, at the conclusion of a user's initial whole-body scan. This would locate each feature on the skin map on a location of the user's body. Then, when subsequent scans are performed, newer images are located by relying on the alignment of the newer images to the older skin map.

SLAM is a technique (sometimes used by robots and autonomous vehicles) to build up a map within an unknown environment, or to update a map within a known environment, while at the same time keeping track of current location. Mapping refers to the problem of determining what the total skin surface looks like (i.e., a map of the skin); in the SLAM context, location refers to the problem of locating the scanner's position on the skin surface (i.e., where the scanner is on the map of the skin). In a SLAM method, the mapping and location tasks can be performed iteratively. When using the scanner system with a SLAM method, SLAM can be implemented in real time, as the user is scanning his or her skin, or can be implemented in an offline mode, i.e., using images recorded during a scan for SLAM, after the scan has been completed. The offline mode can be preferred because it does not require rapid processing as the scan proceeds.

In particular, SLAM can be used for its locating functions, i.e., informing the user where he or she should look on his or her body for the area shown in a particular image. In some embodiments, the scanner includes one or more skin-facing cameras that record close-up and/or high resolution images of the skin and one or more additional, secondary cameras, for example mounted on a side handle of the scanner, to record images of the body from an elevated angle of view. The second camera can be configured to record images with a wider field of view than the skin-facing camera. In this embodiment, the system uses SLAM in a manner analogous to its use in, for example, a robot exploring an unknown building. In this case the user's body corresponds to the building. Inside the building, SLAM compares the features from different images and links the images to create a map based linked features. On a user's body, SLAM compares the body parts (e.g., typically larger than the skin features discussed above; here, for example, SLAM uses e.g., fingers, toes, arms, or added markers) in different images to link them to create the map. These large features help create a 3D body model. Optionally, one or more external marks are put near or on the user's the body to serve as features for SLAM. The 3D body model generated from the secondary camera(s) can have the appearance of a human body.

The system can use the relationships between the 3D body model and the skin map to create an image viewing system that allows the user to view a high-level map of the body, then select an area for viewing in finer and finer detail; or in reverse, to view a close-up image and then zoom out to find where on the body that close-up image was recorded.

The user can interact with system 100 via at least two user operable systems: one is user control 160 located on scanner 105; another is a software user interface provided on computer 101. User control 160 can be a simple control, e.g., a simple button that the user operates to initiate or terminate a scan. In some cases, more complex controls can be provided on scanner 105.

The software user interface (UI) can be provided as a smartphone app, a computer software program, an online platform, an interface on a dedicated console, or other means of allowing a user to interact with software, or a combination of these. In some embodiments, the primary UI is provided as a smartphone app, and a computer software program and/or online platform serves as a secondary UI. Thus the user can access and manipulate data via one or more software UIs.

The software UI acts as a front-end for user control of underlying software. When system 100 is implemented for home use, the software UI can be simple in design and operation, even if the underlying software is complex and completes numerous sophisticated tasks. Among the functions of the software are: to record new images; store images; organize images by date and time recorded, the identity of the user, and the position on the user's skin where the image was recorded; perform location of new images (i.e., identify older and newer images that depict the same area of the user's skin); compare older and newer images of the same area to identify changes in the appearance of the user's skin, including the identification of new skin lesions or other marks and identification of changes to existing lesions or other marks.

In some embodiments, the software can present the user with a mosaic image of their skin, highlighting locations where existing, new, unchanged, or changed marks or lesions appear; this mosaic presented to the user can be referred to as a mole map. If desired, the user can provide his or her own annotations to the mole map. In other embodiments, the software can present the user with a list of skin marks or lesions. The software can allow a user to select a particular mark or lesion from the mole map or list, and review a series of images of that mark or lesion that were recorded at different times. The software can perform automatic comparisons of an area of skin, and provide an alert to the user if the software detects a change such as the appearance of a new mark or lesion, or a change in the size, shape, color, or other property of a mark or lesion. In some embodiments, the system is configured to also alert the user's doctor, dermatologist, or other health care provider, when such a change is detected.

In some embodiments, the system can be used by more than one user. In this case, before initiating a scan, the user identifies him- or herself to the system (e.g., with a username and password), so that the system can separately track the marks and lesions of each different user. This allows the system to be used, for example, by multiple members of the same household; or in a clinical context, by many different patients seen by a health care provider.

Other embodiments are within the scope of the following claims.

What is claimed is:

1. A handheld scanner system comprising:
   a handheld scanner device comprising:
   a skin contact surface;
   a primary camera spaced a distance apart from the skin contact surface, such that when the skin contact surface is contacted to a user's skin, the primary camera records a close up image of a desired area of the user's skin; and
   an illumination source spaced a distance apart from the skin contact surface, such that when the skin contact surface is contacted to a user's skin the illumination source can illuminate the desired area of the user's skin; and
   a computer system operably connected to the handheld scanner device via a data connection and provided with computer-readable instructions configured to cause the computer system to record and store a first plurality of images of one or more desired areas of the user's skin at an earlier time; and to cause the system to record and store a second plurality of images of the one or more desired areas of the user's skin at a later time, create a skin map based on second plurality of images, and while the skin map is being created, generating a 3D body model,
   wherein the computer-readable instructions are further configured to cause the system to use a secondary camera and a SLAM algorithm to locate a mark on the user's skin.

2. The system of claim 1, wherein the computer-readable instructions are further configured to cause the system to compare the first plurality of images and the second plurality of images of the one or more desired areas of the user's skin.

3. The system of claim 1, wherein the computer-readable instructions are further configured to cause the system to detect changes in each of the one or more desired areas of the user's skin based on a comparison.

4. The system of claim 1, wherein the computer-readable instructions are further configured to cause the system to locate a mark or lesion on the user's skin.

5. The system of claim 1, the computer-readable instructions are further configured to cause the system to record and store the first plurality of images and second plurality of images as overlapping areas of the user's skin.

6. The system of claim 1, wherein the computer-readable instructions are further configured to cause the system to create a mosaic image of the user's skin from the first plurality of images and second plurality of images as overlapping areas of the user's skin.

7. The system of claim 1, wherein the primary camera records a second close up image of the desired area of the user's skin as one of the first plurality of images from a different perspective.

8. The system of claim 7, wherein computer-readable instructions are configured to cause the system to construct a 3D image based on the first and second plurality of images of the desired area of the user's skin.

9. The system of claim 1, wherein the data connection is a wireless data connection.

10. The system of claim 1, wherein the skin contact surface includes one or more rollers configured to measure a direction and a distance traveled over a user's skin.

11. The system of claim 1, wherein the illumination source includes one or more LEDs.

12. A method of detecting changes in a person's skin comprising:
    contacting a skin contact surface of a handheld scanner device to a user's skin;
    recording and storing a first plurality of images of one or more desired areas of the user's skin at an earlier time from the handheld scanner device;
    creating a first skin map with the first plurality of images;

recording and storing a second plurality of images with a secondary camera of the one or more desired areas of the user's skin at a later time from the handheld scanner device;

creating a second skin map with the second plurality of images;

while the second skin map is being created, generating a 3D body model;

comparing the first plurality and second plurality of images of the one or more desired areas of the user's skin;

detecting changes in each of the one or more desired areas of the user's skin based on the comparison of the first plurality and second plurality of images;

identifying a location of the first and the second plurality of images in the 3D body model; and alerting the user if any changes are detected and recording an image of a part of the user's body, the image acquired from the secondary camera, and using the image of the part of the user's body and a SLAM algorithm to locate a mark on the user's skin.

13. The method of claim 12, wherein the handheld scanner device includes:
a primary camera spaced a distance apart from the skin contact surface, such that when the skin contact surface is contacted to a user's skin, the primary camera can record a close up image of a desired area of the user's skin; and
an illumination source spaced a distance apart from the skin contact surface, such that when the skin contact surface is contacted to a user's skin the illumination source can illuminate the desired area of the user's skin;
wherein the handheld scanner device operably connects to a computer system provided with computer-readable instructions via a data connection.

14. The method of claim 13, further comprising recording a second close up image of the desired area of the user's skin from a different perspective, and constructing a 3D image based on the first and second plurality of images of the desired area of the user's skin.

15. The method of claim 12, wherein recording and storing a first or second plurality of images includes moving the handheld scanner device over the user's skin while the skin contact surface remains in contact with the user's skin.

16. The method of claim 12, further comprising locating a mark or lesion on the user's skin based on the first or second plurality of images.

17. The method of claim 12, wherein recording and storing a first plurality of images of one or more desired areas of the user's skin includes recording and storing images of overlapping areas of the user's skin.

18. The method of claim 12, further comprising creating a mosaic image of the user's skin from images of overlapping areas of the user's skin.

19. The method of claim 12, wherein the skin contact surface includes one or more rollers configured to measure a direction and a distance traveled over a user's skin and further comprising measuring a direction and a distance traveled by the handheld scanner device over the user's skin.

* * * * *